United States Patent
Yakubov

(10) Patent No.: US 7,217,699 B2
(45) Date of Patent: May 15, 2007

(54) COMPOSITIONS COMPRISING GENOME SEGMENTS AND METHODS OF USING THE SAME

(75) Inventor: Leonid A. Yakubov, Philadelphia, PA (US)

(73) Assignee: Panagenic International, Inc., Philadelphia, PA (US)

( * ) Notice: Subject to any disclaimer, the term of this patent is extended or adjusted under 35 U.S.C. 154(b) by 425 days.

(21) Appl. No.: 09/753,892

(22) Filed: Jan. 3, 2001

(65) Prior Publication Data

US 2002/0025522 A1 Feb. 28, 2002

Related U.S. Application Data

(60) Provisional application No. 60/174,155, filed on Jan. 3, 2000.

(51) Int. Cl.
*A61K 48/00* (2006.01)

(52) U.S. Cl. ......................... 514/44; 435/455

(58) Field of Classification Search ................. 514/44; 435/455

See application file for complete search history.

(56) References Cited

U.S. PATENT DOCUMENTS

| | | | | |
|---|---|---|---|---|
| 3,803,116 | A | * 4/1974 | Sekiguchi et al. | 530/322 |
| 5,176,203 | A | 1/1993 | Larzul | 165/61 |
| 5,302,389 | A | 4/1994 | Kripke et al. | 424/94 |
| 5,352,458 | A | 10/1994 | Yarosh | 424/450 |
| 5,470,577 | A | 11/1995 | Gilchrest et al. | 424/450 |
| 5,589,369 | A | 12/1996 | Seidman et al. | 435/172.3 |
| 5,792,633 | A | 8/1998 | Schiestl et al. | 435/172.3 |
| 5,795,972 | A | 8/1998 | Kmiec | 536/23.1 |
| 5,955,059 | A | 9/1999 | Gilchrest et al. | 424/59 |
| 5,998,382 | A | 12/1999 | Furth et al. | 514/44 |
| 6,010,908 | A | 1/2000 | Gruenert et al. | 435/463 |
| 6,033,880 | A | 3/2000 | Haff et al. | 435/91.1 |
| 6,093,392 | A | 7/2000 | High et al. | 424/93.2 |
| 6,093,567 | A | 7/2000 | Gregory et al. | 435/320.1 |

OTHER PUBLICATIONS

Yáñez et al. "Therapeutic gene targeting," Gene Ther. 5: 149-159, Feb. 1998.*
Riele et al., "Highly efficient gene targeting in embryonic stem cells through homologous recombination with isogenic DNA constructs," Proc. Natl. Acad. Sci. USA, 89: 5128-5132, Jun. 1992.*
Porter, A.C.G., "Correcting a deficiency," Mol. Ther. 3 (4): 423-424, 2001.*
Ledoux, L., "Uptake of DNA by living cells," Prog. Nucleic Acid Res. Mol. Biol. 4:231-267, 1965.*
Yoon et al., "Bases for failure to induce transformation in vivo with exogenous, homologous DNA in mice, autoradiographic investigation of incorporation of exogenous DNA labeled with 3H-thymidine into germ cells," Expt. Cell. Res. 34: 599-602, 1964.*
Karpfel et al., "Chromosome aberrations produced by deoxyribonucleic acids in mice," Expt. Cell. Res. 32 : 147-216, 1963.*
Wilczok et al., "DNA repair of radiation damage. I. DNA adminstered to rats after whole-body irradiation," Int. J. Rad. Biol. Rel. Stud. Phys. Chem. Med. 9 (3): 201-211, 1965.*
Ledoux et al., "Penetration and fate of exogenous DNA into cells of normal and irradiated mammalian tissues," U.S. Clearinghouse Fed. Sci. Tech. Inform. No. 715018, 1970.*
Taubes, G. "The strange case of chimeraplasty," Science 298: 2116-2120, Dec. 13, 2002.*
Deng et al., "Reexamination of gene targeting frequency as a function of the extent of homologoy between the targeting vector and target locus," Mol. Cell. Biol. 12 (8): 3365-3371, Aug. 1992.*
Bearn et al., "Failure of deoxyribonucleic acid to produce pigment changes in the albino rat," Exp. Cell. Res. 17 (3): 547-549, Jun. 1959.*
Szybalska et al., "Genetics of human cell lines, IV. DNA-mediated heritable transformation of a biochemical trait," Proc. Natl. Acad Sci. USA 48: 2026-2034, 1962.*
Anderson et al., "Cyclophosphamide: review of its mutagenicity for an assessment of potential germ cell risks," Mutat. Res. 330: 115-181, 1995.*
Kawabata et al., "The fate of plasmid DNA after intravenous injection of mice: involvement of scavanger receptors in its hepatic uptake," Pharm. Res. 12 (6): 825-830, 1995.*
Sigma Molecular Biology Catalog, p. 60, 1993.*
2000/2001 Sigma Catalog, p. 319, received by PTO on Feb. 15, 2000.*
Alexeev, V ., et al., "Stable and inheritable changes in genotype and phenotype of albino melanocytes induced by an RNA-DNA oligonucleotide," *Nature Biotechnology*, 1998, 16, 1343-1346.
Baccetti, B., et al., "Apoptosis in human ejaculated sperm cells (notulae seminologicae 9)," *J. Submicrosc Cytol Pathol.*, 1996, 28(4), 587-596, *PubMed Query*, http://www.ncbi.nlm.nih.gov/htbin-post/Entrez/query?db=, 1 page, English abstract.

(Continued)

*Primary Examiner*—Scott D. Priebe
(74) *Attorney, Agent, or Firm*—Pepper Hamilton LLP

(57) ABSTRACT

Methods of treating an individual who has a disease or disorder associated with one or more genetic mutations or undesirable alleles in genomic DNA of the individual, or preventing an individual from developing a disease or disorder associated with one or more genetic mutations or undesirable alleles in genomic DNA of the individual, by replacing a segment of genomic DNA that has a mutated sequence or undesirable allele with a corresponding segment of DNA that has a non-mutated sequence or desirable allele, are disclosed. Methods of inducing tolerance and preventing transplant rejection in a recipient, methods of inducing tolerance and or reducing allergies are disclosed and method of increasing fertility in a woman are disclosed. Each of the methods comprises replacing a segment of genomic DNA in an individual with a corresponding segment of DNA from another. An apparatus for doing large scale PCR preparations is disclosed. Pharmaceutical compositions that comprise a plurality of polynucleotide molecules which collectively comprise an essentially complete genome in polynucleotide molecules having about 100–3000 nucleotides are disclosed.

8 Claims, 5 Drawing Sheets

OTHER PUBLICATIONS

Bendich, A., et al., "Information transfer and sperm uptake by mammalian somatic cells," *Nucl. Acids Res. M.B.*, 1976, 17, 43-75.

Bennett, R.M., "As nature intended? The uptake of DNA and oligonucleotides by eukaryotic cells," *Antisense Res. And dev.*, 1993, 3, 235-241.

Billingham, R.E. "Actively acquired tolerance of foreign cells." Nature 172: 603-606, 1953.

Gershenzon, S.M., "The selectivity of the mutagenic action of DNA and other polynucleotides," *Zh Obshch Biol.*, 1996, 57(6), 661-683, PubMed, http://www.ncbi.nlm.nih.gov:80/entrez/que...db=PubMed &list_uids=dopt=abstract, 1 page, English abstract.

Gershenson, S.M., "Induction of directed mutations in drosophila melanogaster," *Doklady Akademii Nauk*, 1939, vol. XXV(3), 225-227, English abstract.

Gershenson, S.M., "Viruses as environmental mutagenic factors," *Mutation Research*, 1986, 203-213.

Guvakova, M.A., et al., "Phosphorothioate oligodeoxynucleotides bind to basic fibroblast growth factor, inhibit its binding to cell surface receptors, and remove it from low affinity binding sites on extracellular matrix," *J. Biochemical Chem.*, 1995, 270(6), 2620-2627.

Immunological Tolerance, *Chapter 14*, 187-198.

Kaledin, V.I., et al., "A new strain of a/he mice hepatoma (hepatoma "A")," *Institute of Cytology and Genetics*, 1974, 3 pages, English abstract.

Lederman, S., et al., "Polydeoxyguanine motifs in a 12-mer phosphorothioate oligodeoxynucleotide augment binding to the v3 loop of HIV-1 gp120 and potency of HIV-1 inhibition independently of G-tetrad formation," *Antisense & Nucleic Acid Drug Dev.*, 1996, 6, 281-289.

Morrison, C., et al., "Extrachromosomal recombination occurs efficiently in cells defective in various DNA repair systems," *Nucleic Acids Res.*, 1996, 24(11), 2053-2058.

Pfeiffer, P., "The mutagenic potential of DNA double-strand break repair," *Toxicol. Letts.*, 1998, 96-97, 119-129.

Ridge, J.P., et al., Neonatal tolerance revisited: turning on newborn T cells with dendritic cells, *Science*, 1996, 271, 1723-1726.

Rykova, E.Y., et al., "Serum immunoglobulins interact with oligonucleotides," *FEBS Lets.*, 1994, 344, 96-98.

Scott, D.W., "Tollerance," *Encyclopedia of Imm.*, New York, 1992, 1481-1487.

Simon, A.R., et al., "Efficacy of adhesive interactions in pig-to-human xenotransplantation," *Immunology Today*, 1999, 20(7), 323-329.

Telenius, H., et al., "Degenerate oligonucleotide-primed PCR: General amplification of target DNA by a single degenerate primer," *Genomics*, 1992, 13, 718-725.

Tonkinson, J.L., et al., "Cellular pharmacology and protein binding of phosphoromonothioate and phosphorodithioate oligodeoxynucleotides: A comparative study," *Antisense Res. And Dev.*, 1994, 4, 269-278.

Vlassov, V.V., et al., "Penetration of oligonucleotides into mouse organism through mucosa and skin," *FEBS 12763*, 1993, 327(3), 271-274.

Vlassov, V.V., et al., "Iontophoretic delivery of oligonucleotide derivatives into mouse tumor," *Antisense Res. And Dev.*, 1994, 4, 291-293.

Vlassov, V.V., et al., "Transport of oligonucleotides across natural and model membranes," *Biochimica et Biophysica Acta*, 1994, 1197, 95-108.

Wagner, T.E., et al., "Human sperm chromatin has a nucleosomal structure," *Arch. Androl.*, 1981, 7, 251-257.

Yakubov, L.A., et al., "Oligonucleotide-cell surface protein complexes trafficking into cell nuclei.," *Int. union of Biochem. & Molecular biology & US Nat. Cancer Inst.*, Millennium Conference on Nucleic Acid Therapeutics, Jan. 8-11, 2000, p. 42.

Yakubov, L.A., et al., "Mechanism of oligonucleotide uptake by cells: involvement of specific receptors," *Proc. Natl. Acad. Sci. USA*, 1989, 86, 6454-6458.

Yakubov, L.A., et al., "The extracellular domain of CD4 receptor possesses a protein kinase activity," *FEBS Lett. 431*, 1998, 45-48.

Yakubov, L.A., "Inhibition of reporduction of HIV virus by anionic dyes,", *Doklady Akademii Nauk*, 1996, 347(5), 696-698, English abstract.

Yakubov, L.A., et al. , "Specific cell surface proteins participate in transport of nucleic acids into cells," *Doklady Akademii Nuak*, 1998, 361(4), 550-553, English abstract.

* cited by examiner

SEQUENCE LISTING

<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<221> NAME/KEY: misc_feature
<223> OTHER INFORMATION: synthetic primer
<221> NAME/KEY: misc_feature
<222> LOCATION: (11)..(16)
<223> OTHER INFORMATION: N is any Nucleotide

<400> SEQUENCE: 1
ccgactcgag nnnnnnatgt gg                                           22

COMPOSITIONS COMPRISING GENOME SEGMENTS AND METHODS OF USING THE SAME

CROSS REFERENCE TO RELATED APPLICATIONS

This application claims priority to U.S. Provisional Application No. 60/174,155 filed Jan. 3, 2000, which is incorporated herein by reference.

FIELD OF THE INVENTION

The present invention relates to compositions and methods of treating individuals with diseases and disorders associated with genetic mutations. According to the present invention, DNA is administered to individuals who take it up and replace DNA with mutated sequences with DNA with non-mutated sequences or substitute existing set of alleles to a different one. The present invention also relates to compositions and methods for preventing and treating infections, allergies, transplant rejections and infertility.

BACKGROUND OF THE INVENTION

Every cell of an organism contains genomic DNA that keeps encoded information about all proteins of all cells of the organism and eventually about the whole organism and its development. Initially this genomic DNA is identical in all cells of an organism. But as the organism grows genomic DNA of every cell becomes subjected to mutational pressure due to environmental factors and mistakes of cellular replication and repair machinery. The known cellular DNA repair mechanisms replace damaged or incorrect DNA bases and rejoin ends of DNA after single-strand and double-strand breaks immediately after mutational events. They can also employ the second DNA chain as a template. When the damage is rather long and affects both DNA chains its repair becomes problematic and the damage results in mutation. The double-strand break repair mechanism can itself be a source of mutations (Pfeifer, P., The mutagenic potential of DNA double-strand break repair. 1998, 96–97, 119–129). As mutations are accumulated in the cellular genome they can cause malfunction of some cells or cancerous transformation.

Environmental mutagenic factors and errors of cellular replication and repair are sources of somatic cell mutations. It has been suggested that gradual accumulation of mutations in cells can cause multi-step cancer transformation. Somatic mutations are considered to be the main cause of aging. Mutations may also induce development of some hereditary associated diseases such as cardio-vascular diseases, high blood pressure, rheumatoid arthritis, and diabetes.

The genetic, multi-mutational nature of cellular cancer transformation and cancer itself suggests that methods of cancer therapy should be directed to the cause of the disease and particularly targeted to the treatment of mutations. Methods for fixing definite point mutations in cells have been suggested (U.S. Pat. No. 5,795,972 issued to Kmiec on Aug. 18, 1998, which is incorporated herein by reference) but according to the method, mutations must be precisely identified before each treatment. Because not a single mutation has been 100% proven to cause a cancer, the development of these methods requires additional fine and time-consuming research. There is a need for methods which can be applied based upon the current knowledge underlying the causes of cancer.

Applying DNA fragments locally has been suggested for treatment of precancerous conditions in skin of patients and for tanning stimulation (U.S. Pat. No. 5,955,059 issued to Gilchrest, et al., on Sep. 21, 1999; and U.S. Pat. No. 5,470,577 issued to Gilchrest, et al., Nov. 28, 1995, both of which are incorporated herein by reference). No sequences or sources of DNA are specified. Rather, the patent suggests that 'any appropriate sources' DNA natural or synthetic, for example, salmon DNA with the length from 200 to mono-nucleotides and nucleosides including dimers, the most potent agents in their tests can be used.

Another method to activate DNA repair in cells is offered including delivery of enzymes participating in DNA repair into skin cells (U.S. Pat. No. 5,352,458 issued to Yarosh, Oct. 4, 1994; and U.S. Pat. No. 5,302,389 issued to Kripke, et. al., Apr. 12, 1994, both of which are incorporated herein by reference). However the latter methods do not suggest fixing of already established or inherited mutations.

There remains a need for methods of correcting genetic mutations. There remains a need for treating individuals who have diseases and disorders associated with genetic mutations. There remains a need to replace undesirable alleles with desirable alleles. There is a further need for methods for inducing tolerance to prevent transplant rejection. There is a further need for methods for inducing tolerance to treat and prevent allergies. There is a need for methods for increasing fertility.

SUMMARY OF THE INVENTION

The present invention arises from the surprising discovery that when an entire genome is administered to an individual in the form of a plurality of polynucleotide molecules that are fragments of genomic DNA, the polynucleotide molecules will circulate, be taken up by cells and translocate to the nucleus of the cells where they will recombine by homologous recombination with the genomic DNA of the cell. Accordingly, genetic defects can be corrected by administering an entire genome to an individual in the form of polynucleotide molecules that are fragments of genomic DNA that are free of the genetic defect. Individuals with diseases and disorders associated with genetic mutations can be effectively treated by the present invention.

Human genomic DNA fragments are used for treating cancer and other diseases caused by mutations. Nucleic acid molecules derived from "healthy" donor DNA is administered to the patient. The nucleic acid molecules correct mutational changes in cells via homologous recombination with mutated genomic sequences. This mechanism modifies allelic genes and in this way an antigenic structure of organism in accordance with composition of administered nucleic acid molecules. The present invention is useful for induction of immunological tolerance at transplantation or pregnancy.

The present invention relates to methods of treating individuals who have diseases or disorders associated with a genetic mutation or undesirable allele in genomic DNA and to methods of preventing individuals from developing diseases or disorders associated with a genetic mutation or undesirable allele in genomic DNA. According to the invention a segment of genomic DNA that has a mutated sequence or undesirable allele is replaced with a corresponding segment of DNA that has a non-mutated sequence or desirable allele. The methods comprise the step of administering to the individual an effective amount of a plurality of polynucleotide molecules that are free of vector sequences. The plurality of polynucleotide molecules collectively comprises an essentially complete genome in polynucleotide molecules having about 100–3000 nucleotides, and includes a polynucleotide molecule which comprises a non-mutated sequence or desirable allele corresponding to the genetic mutation or undesirable allele in the genomic DNA of the cell in the individual. At least some of the plurality of polynucleotide molecules including the polynucleotide molecule which comprises the non-mutated sequence or desirable allele are taken up by the cell of the individual which has the genetic mutation or undesirable allele in genomic DNA, transported to the nucleus of the cell, and recombine with the genomic DNA of the cell by homologous recombination. The mutated sequence or undesirable allele of genomic DNA of the cell is replaced by the non-mutated sequence or desirable allele to correct the genetic mutation in the genomic DNA or incorporate the desirable allele into the genomic DNA.

The present invention relates to methods of inducing tolerance and preventing transplant rejection in an individual comprising the steps of administering to the individual an effective amount of a plurality of polynucleotide molecules that are free of vector sequences. The plurality of polynucleotide molecules collectively comprises an essentially complete genome of the donor in polynucleotide molecules having about 100–3000 nucleotides. At least some of the plurality of polynucleotide molecules are taken up by the cell of the individual, are transported to the nucleus of the cell, and recombine with the genomic DNA of the cell by homologous recombination. The genomic DNA of the individual is replaced by genomic DNA of the donor and tolerance is induced and transplant rejection is reduced in the individual.

The present invention relates to methods of inducing tolerance and treating allergies in an individual comprising the steps of administering to the individual an effective amount of a plurality of polynucleotide molecules that are free of vector sequences. The plurality of polynucleotide molecules collectively comprises an essentially complete genome of the donor in polynucleotide molecules having about 100–3000 nucleotides. At least some of the plurality of polynucleotide molecules are taken up by the cell of the individual, are transported to the nucleus of the cell, and recombine with the genomic DNA of the cell by homologous recombination. The genomic DNA of the individual is replaced by genomic DNA of the donor and tolerance is induced and allergies are reduced in the individual.

The present invention further relates to methods of increasing fertility in a woman. The methods comprise the step of administering to the woman an effective amount of a plurality of polynucleotide molecules that are free of vector sequences. The plurality of polynucleotide molecules collectively comprises an essentially complete genome of a prospective father in polynucleotide molecules having about 100–3000 nucleotides. At least some of the plurality of polynucleotide molecules are taken up by cells of the woman, transported to the nucleus of the cell, and recombine with the genomic DNA of the cell by homologous recombination. Genomic DNA of the woman is replaced by genomic DNA of the prospective father and fertility is improved in the woman.

The present invention relates to methods of preventing or reducing graft versus host disease in a recipient comprising the steps of administering to the donor an effective amount of a plurality of polynucleotide molecules that are free of vector sequences. The plurality of polynucleotide molecules collectively comprises an essentially complete genome of the recipient in polynucleotide molecules having about 100–3000 nucleotides. At least some of the plurality of polynucleotide molecules are taken up by the cells of the recipient, transported to the nucleus of the cell, and recombine with the genomic DNA of the cell by homologous recombination. The genomic DNA of the donor is replaced by genomic DNA of the recipient. Following transplantation/grafting, the level of graft versus host disease is reduced or prevented.

The present invention relates to methods of introducing one or more desirable alleles into livestock which contains undesirable alleles comprising the steps of administering to the livestock an effective amount of a plurality of polynucleotide molecules that are free of vector sequences. The plurality of polynucleotide molecules collectively comprises an essentially complete genome of the livestock species in polynucleotide molecules having about 100–3000 nucleotides including the desirable alleles. At least some of the plurality of polynucleotide molecules are taken up by the cells animal, transported to the nucleus of the cell, and recombine with the genomic DNA of the cell by homologous recombination. The undesirable alleles in the genomic DNA of the animal is replaced by the desirable alleles.

The present invention relates to an apparatus for doing large scale PCR preparations. The apparatus comprises a reaction tube that has an inner diameter of 3 mm or more, at least one pump for continuously supplying of reagents to the reaction tube, four temperature chambers and a collection vessel. The reagents are combined and enter the reaction tube by action of the pump. The reaction tube comprises a series of reaction tube lengths which alternately pass through each of the four temperature chambers to produce a cycle segment, such that a length of the reaction tube passes through the first temperature chamber, a length of the reaction tube passes through the second temperature chamber, a length of the reaction tube passes through the third first temperature chamber, a length of the reaction tube passes through the fourth temperature chamber to produce a cycle segment. The reaction tube comprises at least twenty consecutive cycle segments and is connected to the collection vessel following the last cycle segment.

The present invention relates to pharmaceutical compositions that comprises, in a pharmaceutically acceptable carrier, a plurality of polynucleotide molecules which collectively comprise an essentially complete genome in polynucleotide molecules having about 100–3000 nucleotides.

BRIEF DESCRIPTION OF THE DRAWINGS

FIG. 1A contains six autoradiograms; in each lane C designates the control human breast cancer cells BT474, ovarian carcinoma cells OVCAR5 and promyelocytic leukemia cells HL60; each lane D designates the same cells treated for 2 weeks with DNA preparations (2 μg/well); each lane Ch designates the same cells treated for 2 weeks with chromatin preparations (2 μg of DNA per well). Equal protein amounts of cell lysates were electrophoresed in SDS-PAAG and transferred to nitrocellulose membranes by Western blotting procedure. The membranes were incubated with specific antibodies to proteins Erb-B2, C-Myc and Cyclin D1, washed in buffer and incubated with secondary antibodies conjugated with HRP according to protocols of Santa Cruz Biotech. Co. The membranes were then washed and developed with Luminol reagent and exposed to X-ray film. FIG. 1A shows specific protein expression, X-ray films

DESCRIPTION OF PREFERRED EMBODIMENTS OF THE INVENTION

Figure 1A:
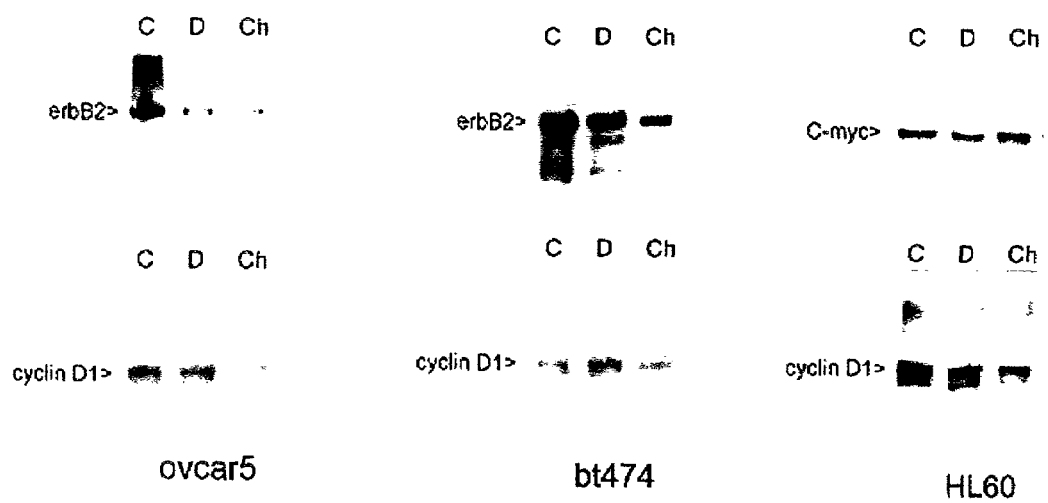
FIG. 1A shows changes in specific protein expression in human cancer cells induced by preparations of human DNA. Three assays were run on each of three cancer cell types (human breast cancer cells BT474, ovarian carcinoma cells OVCAR5 and promyelocytic leukemia cells HL60) and expression was tested of proteins associated with cancer, erbB2 for BT474 and OVCAR5 cells, c-myc for HL60 cells and cyclin D1 for all three cell types.

The mechanisms of entering of oligo- and polynucleotides into living organisms, their distribution between tissues and organs, and particularly the methods of their penetration into living cells have been studied. Specific cell surface proteins have been found to bind to nucleic acid molecules and deliver them into the acidic vesicular endosomal compartment inside cells and further on into cell nuclei. Oligonucleotides and polynucleotides have been shown to enter cells via a saturable, partially reversible receptor-mediated endocytosis mechanism. It has been observed that nucleic acids can enter a mammalian organism via gastrointestinal and other mucosas or even through the skin. Having been injected intravenously or intraperitoneally they were delivered systemically by circulation to all cells of the organism.

An even more exciting discovery about these receptors has now been made. The same proteins that bind oligonucleotides on the cell surface are responsible for their delivery into the cell nucleus. Thus nuclear oligonucleotide delivery was found to be a multi-step process employing the cell surface receptors and resulting in reversible redistribution of the receptors in the cell to mostly nuclear localization and the process was activated by extracellular oligonucleotides.

Nucleic acid fragments are normally present in plasma and tissue fluids. They are constantly produced in organisms as a result of cellular death via apoptosis (programmed cell death) and necrosis of cells and consist mainly of the fragmented genomic DNA complexed with nuclear proteins. This fragmented genomic DNA can be taken up by cells of the body, then transported to cellular nuclei and finally can be employed as an external DNA standard for repair of mutations in cells via homologous recombination of the delivered DNA fragments with cellular genomic DNA.

Although the present invention is expressly not intended to be limited by any theory, the data suggest a possible reason related to the discoveries underlying the present invention. The data suggest that there exists a global genomic DNA repair system which uses extracellular DNA fragments from blood circulation or surrounding tissue fluids as a standard for genomic DNA correction in cells by means of homologous recombination, and which works continuously in every cell of the human body although it is unclear yet to what extent this mechanism resists mutational changes of the cellular genome. The global genomic repair system appears to have three main parts or steps of action: i) generation of extracellular fragmented genomic DNA in an organism, ii) cellular uptake and nuclear delivery of the nucleic acid fragments, and iii) homologous recombination of the fragments with genomic DNA. The system stands guard over invariability of the genome and eliminates mutations in every cell of an organism.

Although extracellular nucleic acids can have some misspelled sequences from the death of rare mutated but unrepaired cells, the percentage of such sequences compared to the 'correct' DNA is usually extremely low. However if mutated cells are numerous, they themselves may become a source of mutated plasma DNA (especially if these cells undergo increased apoptosis or necrosis). This can result in multiple mutations of cells in the body. The quantity of mutations will depend on the percentage of mutant DNA in the plasma DNA reservoir. The death of new mutated cells will produce mutated DNA that will increase the proportion of mutated DNA in plasma DNA. This in turn will increase the number of mutated cells via recombination with cellular DNA. An increase in mutated sequences in plasma DNA will be followed by an increase in the proportion of mutated cells in the organism and may further lead to multiple mutations in cells of the body. Depending on how a mutation affects certain properties of cells (e.g. rate of multiplication or tendency towards apoptosis or necrosis) the percentage of the mutated DNA in plasma DNA will either increase or decrease. Since many different mutations can e displayed in cellular populations of an organism, the mutated sequences will be presented in extracellular DNA of circulation and tissue fluids in corresponding proportions with corrections to the relative rates of cell death in mutated cells. Because such DNA fragments will simultaneously perform repair of mutations in some cells and induce mutations in others, all cells of the organism will be in a state of mobile mutational equilibrium. This equilibrium can be shifted by a variety of factors, such as the possibility for free DNA of the cellular surroundings to play a more important role in the recombination than that of plasma DNA. These processes can change frequencies of mutations in the body and cellular communities and cause gradual drift of the plasma DNA standard. Therefore in light of this theory, cancer and aging may not be diseases of cells or cellular clones, but those of the genome of the organism. If such a global DNA proofreading mechanism exists, any damage or malfunction of its components will result in genetic instability of cells in the organism, accelerating carcinogenesis, premature aging or other disorders.

The theory considered above suggests, that horizontal transfer of genetic material between cells in the body is usually normal state of cellular community. This concerns not only proper inherited genomic DNA but any DNA that happen to be introduced into the body. This DNA will certainly recombine with genomic DNA at cites of homology, and the frequencies (and number of sequences or genes ready to recombine) of recombination will correlate primarily with extent of the relation: high and very high frequencies between DNAs of the same species, lower between remote species and rare between far remote species. Herewith frequencies of recombination for separate homologous genes will be the same regardless of hereditary relations.

Definitions

As used herein, the term "individual" refers to the vertebrate targeted for use of the present invention. Examples of "individuals" contemplated by the present invention include but are not limited to humans, higher order primates, canines, felines, bovines, equines, ovines, porcines, avians, and other mammals.

As used herein, the term "diseases and disorders associated with genetic mutations" refers to: cancer; heart and blood vessel diseases; peripheral blood vessel diseases; autoimmune diseases; diabetic conditions; neurodegenerative conditions; gastroenterological and hepatological diseases; mutagenic pathogen disorders; classic hereditary diseases; disorders due to exposure to mutagenic stimuli; other multifactorial diseases; hereditary predisposition to one of the above-mentioned diseases; and aging As used herein, the term "administration" refers to the delivery of polynucleotide molecules to the individual. The term includes, but is not limited to delivery routes including intramuscularly, intravenously, intranasally, intraperatoneally, intradermally, intrathecally, intraventricularly, subcutaneously, transdermally or topically or by lavage. Modes of administration contemplated by this invention include but are not limited to the use of a syringe, intravenous line, transdermal patch, or needleless injector.

As used herein, the term "segment" refers to a portion of genomic DNA with or without mutations.

As used herein, the term "allele" used in the context of an undesirable allele being replaced with a desired allele refers to the entire gene or a portion of the gene such that following recombination with a portion of the gene, the undesirable allele is replaced with the desirable allele. Accordingly, the polynucleotide molecules used to replace an undesirable allele need not comprise the entire gene but enough of the gene to effectively convert the undesirable allele into a more desirable form.

As used herein, the phrase "plurality of polynucleotide molecules that are free of vector sequences" refers to a composition that comprises multiple different nucleic acid molecules which are fragments or copies of fragments of genomic DNA. The nucleic acid molecules are preferably DNA. The nucleic acid molecules do not include sequences other than genomic sequences. A "plurality of polynucleotide molecules that are free of vector sequences" does not contain any vector sequences such as viral or cell sequences from a vector host.

As used herein, the phrase "each polynucleotide molecule has 100–3000 nucleotides" refers to the number of nucleotide bases on a single strand of a nucleic acid molecule. A double stranded nucleic acid molecule such as a DNA would contain 200–6000 nucleotides as 100–3000 base pairs.

As used herein, the phrase "plurality of polynucleotide molecules collectively comprises an essentially complete genome" refers to the composition, which if assembled would equal a complete genome. The plurality of polynucleotide molecules are a plurality of fragments of genomic DNA or a plurality of copies of fragments of genomic DNA. For example, in some embodiments, a complete genome of genomic DNA is isolated from an individual, such as isolated chromosomal DNA, fragmented into a plurality of fragments by mechanical sheering and/or sonication and/or partial enzymatic digestion and/or restriction endonuclease digestion. Such a fragmented chromosomal isolate collectively comprises an essentially complete genome. Likewise, copies of an entire genome can be made and amplified by polymerase chain reaction using random primers and whole genome chromosomal DNA as a template. The plurality of polynucleotide molecules generated by such amplification techniques "collectively comprises an essentially complete genome" in that essentially the entire genomic DNA is copied and found within any one or more of the several randomly produced amplification products which are copies of fragments of genomic DNA.

As used herein, the phrase "plurality of polynucleotide molecules includes a polynucleotide molecule which comprises a non-mutated sequence corresponding to the genetic mutation in the genomic DNA of the cell in the individual" is meant to refer to the use of genomic DNA chromosomal starting material from sources believed to be free of the mutated sequence which means that the mutated sequence may be present in such low percentage that in a healthy person it does not induce any pathology. For example, autologous starting material derived from a patient at an early age or prior to exposure to mutagenic stimuli may be used. Similarly, starting material derived from a donor who is not believed to be a carrier or otherwise possess the genetic mutation associated with a patient or at least is not suffering from the disease. In some cases, the exact nature of genetic mutation associated with a patient may be unknown and the starting material derived from a donor who is not patient and therefore believed to be free of the genetic mutation. In some cases, the exact nature of genetic mutation associated with a patient may be known and associated with specific cells, such as tumor cells. The starting material may be derived from non-tumor tissue of the patient and therefore believed to be free of the genetic mutation but this may not be the best idea because even non-tumor tissues of the patient may have the predisposition to develop into a tumor.

As used herein, the term "treatment" is meant to refer to stabilization, reduction, or reversal of symptoms or the prevention of further advance of disease, debilitation and death.

Diseases and Disorders

Individuals who have diseases and disorders associated with genetic mutations may be treated by the methods of the invention. As noted above, the diseases include: cancer; heart and blood vessel diseases; peripheral blood vessel diseases; autoimmune diseases; diabetic conditions; neurodegenerative conditions; gastroenterological and hepatological diseases; mutagenic pathogen disorders; classic hereditary diseases; disorders due to exposure to mutagenic stimuli; and other multifactorial diseases.

The present invention allows for the treatment of multifactorial diseases. With some multifactorial diseases, it is necessary to correct several gene mutations at the same time: for example, higher than normal level of cholesterol is mainly caused by genetic factors. While a few genes have been identified whose mutant alleles have large effects on this trait (e.g. LDLR, familial defective apoB-100), variability in cholesterol levels among individuals in most families is influenced by allelic variation in many genes (polymorphisms) as well as environmental exposures.

Examples of cancer include: Bladder cancer; brain and CNS cancer; breast cancer; cancer in children; colorectal, esophageal, eye tumors; head and neck; kidney cancer; leukemia; liver cancer; lung cancer; lymphoma; melanoma and other skin cancers; myeloma; pancreatic cancer; prostate cancer; sarcomas; stomach cancer; and testicular cancer. The present invention may be used to prevent metastasis and particularly effective at early stages of cancer, or in some embodiments at pre-cancerous conditions.

Examples of heart and blood vessel diseases include: coronary heart disease; angina; heart attack; high blood pressure; congestive heart failure; cardiac arrhythmias; sudden cardiac death; heart valve disease; congenital heart defects; and stroke (usually a consequence of blood vessel disorder);

Examples of peripheral blood vessel diseases include: peripheral arterial diseases; arteriosclerosis obliterans; Buerger's disease; Raynaud's phenomenon; aneurysms; peripheral venous disorders: varicose veins; and phlebitis (thrombophlebitis).

Examples of autoimmune diseases includes: Rheumatoid arthritis (RA), multiple sclerosis (MS), Sjogren's syndrome, sarcoidosis, autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis.

Examples of diabetic conditions include Type I and Type II diabetes. In Type I diabetes, also referred to as insulin dependent diabetes mellitus (IDDM), more than 10 different genetic markers have been found to be associated with the disease. In Type II diabetes, also referred to as adult onset or maturity-onset diabetes of the young (MODY) mutations in five different genes, which are code for glucokinase and various transcription factors, have been found to be associated with this form of diabetes.

Examples of neurodegenerative diseases include: Huntington's disease; spinocerebellar ataxias; Alzheimer disease; amyotropic lateral slerosis (ALS) and Parkinson's disease.

Examples of gastroenterological and hepatological diseases include: gastrointestinal malignancies, viral hepatitis, hyperholesterolaemia, alpha 1-antitrypsin deficiency; metabolic diseases of the liver and cystic fibrosis.

Examples of mutagenic pathogen disorders include those shown to be caused by nucleic acids of viral and bacterial or fungal pathogens. The severe infections by some pathogens cause mutational changes in the body of the infected individual. Viruses are etiological agents of many human diseases. Viral nucleic acids have a considerable homology with some human genomic sequences. During acute infections large quantities of viral nucleic acids are detected in tissue fluids and circulation. Viral infections are known to induce some mutations in humans, moreover some viruses can incorporate their sequences in human cellular DNA which causes latent, chronic and slow hidden viral infections. Viral infections, such as rubella, result in genetic lesions causing abnormalities of early development. Human genomic DNA preparations can treat post-viral changes in cellular genome. They are likely to treat all forms of viral infections including acute, latent and chronic forms. HIV, herpes simplex virus, rabies virus, influenza virus, hepatitis A, B and C, rubella are all candidates for this treatment.

Examples of classic hereditary diseases, i.e. typical human genetic diseases, include, but are not limited to: Achondroplasia, Adult Polycystic Kidney Disorder, Alpha Zero Thalassaemia, $Alpha_1$-Anti-trypsin Deficiency, Alpha-Thalassaemia, Beta-Thalassaemia, Color Vision Disorders, Congenital Hypothyroidism, Congenital Malformations, Cystic Fibrosis, Diabetes Mellitus, Duchenne Muscular Dystrophy, Epilepsy, Familial Hypercholesterolemia (FH), Fetal Rubella Syndrome, Fragile X Mental Retardation, Glucose-6-Phosphate Dehydrogenase Deficiency, Glutathione Deficiency, Haemoglobinopathies, Hemochromatosis, Hemophilia A and B, Huntington Disease, Inherited Thrombophilia, Neurofibromatosis, Obesity, Oculo-cutaneous Albinism, Phenylketonuria (PKU), Sickle Cell Disorders, Thalassemia, and Werding-Hoffman Disorder.

Examples of aging as a state of human organism which is characterized by presbyopia, loss of elasticity of skin, wrinkles, hair loss, muscle weakness, fragility of bones, gray hair, flexibility of joints, decline of sexual drive and menopause. One of the main causes of aging is gradual accumulation of mutations in cells of the body. Genomic DNA treatment can prevent and repair mutational changes in cellular genomes. This treatment has a potential to prevent and reverse aging effects in humans.

Examples of disorders due to exposure to mutagenic stimuli include those which result from exposure to ionizing radiation and chemical mutagen exposure.

Examples of other multifactorial diseases includes: dermatological disorders; urological disorders; immunological disorders such as induction of immunological compatibility at transplantations; infertility due to miscarriages; endocrinological disorders; ophtalmological disorders (cataract); otolaryngological disorders; rheumatological disorders; and gynecological disorders.

In some embodiments, the present invention provides the means to correct genetic mutations by replacing mutated sequences with corresponding non-mutated sequences or substitute one set of alleles for a different one. The present invention may be used to replace less desirable alleles with more desirable ones. For example, hair loss can be treated or prevented, hereditary diseases may be considered alleles rather than mutations. Other applications including cosmetic applications may also be allele-based rather than correcting mutations.

The methods of the invention can be applied to animal breeding. DNA preparations of animals with successful allelic composition can be prepared and amplified using this method. When injected in newborn animals or in embryos at early stages of development, these sequences can help accelerate breeding animals with the best properties.

In some embodiments, the present invention provides the means to induce tolerance, reduce transplant rejection and/or graft versus host disease and improve fertility by increasing tolerance/reducing rejection in the mother. In the classical work in early 1950s reported in Billingham et al. (1953) Nature 172(4379):603–606, Medawar and his colleagues found a way to induce artificial tolerance in neonatal mice at allotransplantation via injection of blood lymphocytes from donor to the recipient mouse before transplantation. Later it was found that injections of large amounts of donor splenocytes or bone marrow cells can induce tolerance or diminish the immune response at the transplantation in adult mice. It was suggested that high dose of donor antigens injected caused deaths of lymphocyte clones responsible for the transplant rejection, but a finding that the induced tolerance was unexplainably inheritable complicated the explanation. Recently it was suggested that immune system responds by immunization or tolerance depending of the accompanying presence of some "Danger" signal performed by specific cells (Ridge et al. 1996 Science 271(5256) 1723–6).

Immunologists consider injections of cells to recipient just as injection of some quantity of foreign antigen with following reaction of immune system, while every lymphocyte or splenocyte carries set of genomic DNA, and the real sense of the injection may be just injection of foreign nucleic acids into the body. In the light of the theory disclosed in this application for example, the DNA from injected cells is digested partially, taken up by cells of the body and recombines in areas of homology with host DNA. This can modify some genes in cells of the body, including cells of the immune system, and that will change the cells antigenic properties. After this, the immune system will have no choice but to consider its own cells with changed antigenic structure as proper cells of the organism. Lymphocyte clones responsible for recognition of the new antigen are probably deleted. This new property of the body will certainly have the possibility to be inherited if corresponding genes will be modified at least in part of germ cells.

For better results at allotransplantation physicians use lymphocytes or bone marrow cells injections from the future donor, although sometimes this procedure gives adverse reaction accelerating rejection. When a donor is not known, multiple blood infusions from different persons are administered, to increase allograft survival and diminish immune reaction, although this procedure can allergize the recipient and result in an adverse effect.

Instead of whole cells, according to the present invention, either segments of donor DNA or mixed DNA segments of 10–20 healthy persons are administered. These DNA preparations are neither immunogenic, no toxic and will increase tolerance to allograft.

At xenotransplantation of organs, for example pig's heart to a man, good results are observed when intravenous injections of pig bone marrow cells to the future transplant recipient precede the transplantation procedure. Adverse reaction sometimes results from such infusions. Using pig "DNA" will help to solve this problem and increase xenograft survival. Combined human or recipient DNA injected to a pig donor will minimize or abrogate the graft-versus-host reaction.

According to the invention, induction of tolerance can be used to induce tolerance to allergens in those individuals who have allergies. The administration of donor DNA to an individual who has one or more allergies can introduce alleles that prevent allergic reactions when the individual is exposed to the allergen.

Tolerance of mother to fetus may also be mediated by genetic transformation of a mother's cells with DNA segments of a father's genome originating from sperm ejaculated during sex. Immunologists underline that effect in creation of artificial tolerance by cells injections correlate with number of injected cells to recipient. Some infertility problems or unexpected spontaneous termination of pregnancy can be caused by lack or low level of tolerance created in mother to the fetus because of insufficient quantity of sperm cells injected to women, or problems with possible improper sperm cells degradation, breach of transportation of the DNA segments to circulation, and thus insufficient transformation of mother's cells with the delivered DNA. Such problems may be solved by treating the future mother with prepared segments of the father's DNA, or collected frozen sperm samples of the father, or, if the latter is not possible for some reason, even injections of combined human "DNA" fragments from one or more donors.

Dosage

The dosage administered varies depending upon factors such as: pharmacodynamic characteristics; its mode and route of administration; age, health, and weight of the recipient; nature and extent of symptoms; kind of concurrent treatment; and frequency of treatment.

According to some embodiments of the present invention, the plurality of polynucleotide molecules are administered in an amount based on concentrations of circulating DNA and its half life. According to some embodiments of the present invention, the plurality of polynucleotide molecules are administered in an amount of 10 g per month. DNA in blood of a healthy individual approx. 2–10 ng/ml. That is, the "normal" concentration of circulating DNA in blood is approximately 2–10 ng/ml. According to preferred embodiments of the invention, polynucleotide compositions are administered in at least a quantity sufficient to increase the normal level by approximately 10×. Depending upon the route of administration, the increase in concentration may be a 10× surge if a complete dose is administered in a short period of time, 5–10 minutes, or elevated concentration may be maintained over a longer period of time if the DNA is infused continuously or for a period greater than about ten minutes.

In some embodiments of the present invention, DNA is administered to maintain the concentration in the range of 0.01–6 µg/ml, which corresponds to 0.01–2 µM concentration of a fragment with average length of 500 b.p.

Depending upon the manner in which the plurality of polynucleotides are produced, the size distribution will vary. For the purposes of calculating dosage, the fraction of the composition which includes molecules consisting of about 200–3000 nucleotides is measured. Generally, 80% or more of polynucleotides generated by preparations described herein fall within this size distribution. It is preferred that of the fraction of the composition which includes molecules consisting of about 200–3000 nucleotides, the average size of about 300–1000, preferably about 500 nucleotides.

Polynucleotide compositions which comprise 0.4–16 grams of polynucleotide molecules within the 200–3000 nucleotide size distribution are preferably administered to an adult human patient. In some embodiments, the polynucleotide compositions comprise 0.8–14 grams of polynucleotide molecules within the 200–3000 nucleotide size distribution are preferably administered to an adult human patient. In some embodiments, the polynucleotide compositions comprise 1, 2, 3, 4, 5, 6, 7, 8, 9, 10, 11, 12, or 13 grams of polynucleotide molecules within the 200–3000 nucleotide size distribution are preferably administered to an adult human patient.

In some embodiments, the polynucleotide compositions comprise 0.8–16 grams of polynucleotide molecules within the 300–1000 nucleotide size distribution are preferably administered to an adult human patient. In some embodiments, the polynucleotide compositions comprise 0.8–16 grams of polynucleotide molecules within the 300–700 nucleotide size distribution are preferably administered to an adult human patient.

Since the composition may contain polynucleotides outside the size range, the total amount of polynucleotide may be greater, i.e. up to about 20 grams or more. The dose may be delivered over a period of time, as a divided dose administered in a series of administrations over time or as a divided dose delivered at different sites by multiple routes of administration.

The pharmaceutical compositions according to this aspect of the present invention comprise about 0.4 to 20 g or more of nucleic acid molecules within the 200–3000 size distribution; in some embodiments, about 0.6 to 18 g or more of nucleic acid molecules within the 200–3000 size distribution of DNA; in some embodiments, about 0.8 to 16 g or more of nucleic acid molecules within the 200–3000 size distribution of DNA; in some embodiments, about 1 to 16 g or more of nucleic acid molecules within the 200–3000 size distribution of DNA. In some embodiments of the present invention, the pharmaceutical compositions comprise about 0.4 to 20 g or more of nucleic acid molecules within the 300–2000 size distribution; in some embodiments, about 0.6 to 18 g or more of nucleic acid molecules within the 300–2000 size distribution of DNA; in some embodiments, about 0.8 to 16 g or more of nucleic acid molecules within the 300–2000 size distribution of DNA; in some embodiments, about 1 to 16 g or more of nucleic acid molecules within the 300–2000 size distribution of DNA. In some embodiments, the pharmaceutical compositions according to this aspect of the present invention comprise about 0.4 to 20 g or more of nucleic acid molecules within the 300–1000 size distribution; in some embodiments, about 0.6 to 18 g or more of nucleic acid molecules within the 300–1000 size distribution of DNA; in some embodiments, about 0.8 to 16 g or more of nucleic acid molecules within the 300–1000 size distribution of DNA; in some embodiments, about 1 to 16 g or more of nucleic acid molecules within the 300–1000 size distribution of DNA.

In some embodiments, the calculation of DNA dosage is as follows: 3 ml of human sperm=about 1 mg human sperm DNA (3 ml sperm)×(70×10$^6$ cells/ml)×(5×10$^{-12}$ g [amount of DNA in each spermatozoid])=about 200×5× 10$^6$×10$^{-12}$=1000×10$^{-6}$ g=1 mg human sperm DNA.

If multiplied by 10,000 (by PCR)=10 g DNA can be prepared from a 3 ml sample. 10 g DNA/10×10$^{-12}$ g DNA/cell=10$^{12}$ cells; 10$^{12}$×2000 μm$^3$ (volume of embryo fibroblasts)=2 kg We have roughly estimated quantities in which cells are distributed in the human organism taking into account the fact that in some tissues there are very few or no cells or there are few cells that actively participate in DNA circulation in the organism.

The human body of 70 kg equals:
1) skin+skin fat—20 kg (eqv. 0.2 kg cells)
2) Bones+connective tissues+tendons—30 kg (0.2 kg cells)
3) Blood—7 kg (0.07 kg cells)
4) Muscles—10 kg ¹/₂₀ (0.5 kg cells)
5) Intestine—3 kg ¹/₁₀ (0.3 kg cells)
6) liver 1 kg ½ (0.5 kg cells)
7) Brain 1 kg ¼ (0.25 kg cells)
8) Other glands 1 kg (0.25 kg cells)
Total cells 2.3 kg Routes of Administration According to the present invention, the polynucleotide molecules may be delivered to the individual by any means and mode of administration that will result in the polynucleotides being taken up by cells which contain the genetic mutation associated with the disease or disorder to be treated. In some preferred embodiments, the polynucleotide molecules are administered by: intravenous injection; intramuscular injection; intradermal injection; subcutaneous delivery; intraperatoneal delivery; topical or lavage delivery by application onto different mucosa and/or skin; ingestion per os (with or without stomach neutralization pretreatment or enteric-coating formulation); per rectum; intravaginally; intraocularly; intranasally, intratumorally; intracerebrally, intraocular injection, by inhalation and by delivery to the spinal cord.

In some applications, particularly cosmetic applications such as for treatment of hair loss or age-damaged and/or sun-damaged skin, topical administration is preferred.

The devices and apparatus used can be any of those which are useful to administer the polynucleotide composition by the chosen route of administration. In the case of injections, in addition to syringes, in some embodiments, high powered needleless injection devices or projectile bombardment devices may be used.

Those skilled in the art will perform administration by well known methods including appropriate preparatory and follow up examination.

Regimen

According to the present invention, the polynucleotide molecules may be delivered to the individual by any administration regimen that will maintain sufficient polynucleotide presence such that polynucleotides will be taken up by cells at a level effective to correct genetic mutations. In some preferred embodiments, the polynucleotide molecules are administered continuously. In some embodiments, the polynucleotide molecules are administered hourly. In some embodiments, the polynucleotide molecules are administered daily. In some embodiments, the polynucleotide molecules are administered every other day. In some embodiments, the polynucleotide molecules are administered weekly. In some embodiment, the polynucleotide molecules are administered over the course of 1–26 weeks, preferably 2–13 weeks, preferably 2–8 week, preferably 2–6 weeks and, in some embodiments, more preferably 2–4 weeks.

Formulations

Formulations comprising the polynucleotide molecules are made up according to the mode and site of administration. Such formulation is well within the skill in the art. In addition to nucleic acid molecules, the formulation may also include buffers, excipients, stabilizers, carriers and diluents. Suitable pharmaceutical carriers are described in the most recent edition of *Remington's Pharmaceutical Sciences*, A. Osol, a standard reference text in this field which is incorporated herein by reference.

For parenteral administration, the composition can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

The pharmaceutical compositions according to this aspect of the present invention are formulated according to the mode of administration to be used. In cases where injection is the chosen mode of administration, a sterile, isotonic, non-pyrogenic formulation is used. Generally, additives for isotonicity can include sodium chloride, dextrose, mannitol, sorbitol and lactose. Isotonic solutions such as phosphate buffered saline are preferred. Stabilizers include gelatin and albumin.

DNA can be in the form of real solution as sodium or lithium salt or as complexes with basic proteins such as histones or protamines, or synthetic polycations, or precipitates like calcium phosphate, or can be absorbed on carriers such as hydroxylapatite or some anion exchangers. The DNA may be complexed with either synthetic or natural nuclear proteins or both. Further, it may be single- or double-stranded, linear or circular, relaxed or supercoiled.

For administration in the form of suppositorium DNA can also be formulated as mentioned above (solution, suspension, emulsion, dry powder) in combination with conventionally used inactive base including for instance cocoa butter, starch, methylparaben, propylparaben.

For topical application on skin DNA with commonly used inactive ingredients for lotions, creams and ointments, such as mineral or vegetable oil, propylene Glycol, PEG-Stearate, lecitin, EDTA, methyl/ethylparaben.

For administration in low prophylactic doses DNA solutions in composition of lozenges or tablets for dissolving in mouth.

Source

The plurality of polynucleotide molecules may be obtained by processing genomic DNA from a number of sources. In some embodiments, autologous DNA (self donor) that is collected at the patient's young age or at least before the disease or exposure to irradiation or chemical mutagens is used. In such embodiments, genomic DNA may be "banked" from birth or a young age. According to the invention banked collections of DNA samples may be stored in preparation for use according to the invention. In some embodiments, allogenic DNA, such as from living donors or corpses, is used. In such embodiments, genomic DNA may be "banked" for use by allogenic recipients. According to the invention banked collections of DNA samples may be stored in preparation for use according to the invention. In some embodiments, xenogenic DNA may be used, particularly for induction of immunocompatibility at xenotransplantations.

Examples of sources of DNA are as follows:
Sperm DNA taken from a few healthy donors and mixed (each sample from a healthy donor yields 1 mg DNA);
Autologous DNA is less desirable in some embodiments but may be used in some embodiments;
Placental DNA (1 placenta gives 1–2 g DNA);
Abortive material;
Biopsy (e.g. liver) (0.1 g gives 0.5 mg DNA); and
Peripheral lymphocytes.

DNA is preferably amplified as discussed above and below to yield sufficient quantities for use.

Preparation

DNA may be derived from any nucleated cell. In preferred embodiments, it is derived from peripheral blood lymphocytes, sperm cells, Pap smear, tissue biopsy, placenta, and corpse tissues.

Chromatin is isolated from donor material and fragmented by nuclease digestion and/or sonication and/or mechanical sheering. In some preferred embodiments, DNA may be made from genome DNA by isolating DNA, and amplifying "fragments" using PCR with degenerative primers.

For example, random primer PCR mainly according to Telenius et al (1992) Genomics 13:718–725 which is incorporated herein by reference. Telenius reports 18-mer partially degenerative DOP oligonucleotide primers for random DNA amplification. The typical protocol is as follows: PCR buffer with 0.2 mM $MgCl_2$, 0.2 mM NTP, 2 µM DOP 6-MW, 40 U/ml Taq polymerase. Cycler: 95° C. 5'; 10" 94° C., 10" 53° C., 30" 72° C. (the latter three steps are repeated 30 times), 10' 72° C. Using 1 ng of the DNA in a 50 µl reaction mixture we can get up to 10 µg DNA fragments 200–3000 bp in length. A one liter mixture yields 0.2 g DNA; a 10 liter mixture yields 2 g DNA. For 1 liter mixtures we need 40,000 U Taq polymerase, 100 ml 2 mM NTP (100 mg NTP), 20 ml 100 µM DOP 6 M-W (2 µmol).

Compositions

Another aspect of the invention relates to pharmaceutical compositions that comprise, in a pharmaceutically acceptable carrier a plurality of polynucleotide molecules which collectively comprise an essentially complete genome in polynucleotide molecules having about 100–3000 nucleotides.

In some embodiments, the compositions contain 0.01–16 g of polynucleotides having 200–3000 nucleoitides each. In some embodiments, the compositions contain 0.01–16 g of polynucleotides having 200–3000 nucleotides each with an average length of 300–1000 nucleotides. In some embodiments, the compositions contain 0.01–16 g of polynucleotides having 200–3000 nucleotides each with an average length of 500 nucleotides. In some embodiments, the compositions contains 0.04–16 g of polynucleotides having 200–3000 nucleotides each. In some embodiments, the compositions contain 0.4–16 g of polynucleotides having 200–3000 nucleotides each.

In some embodiments, the compositions contain at least 80% of polynucleotide molecules administered are about 200–3000 nucleotides in length. In some embodiments, the compositions contain at least 80% of polynucleotide molecules administered are about 200–3000 nucleotides in length and have an average length of about 300–1000. In some embodiments, the compositions contain at least 80% of polynucleotide molecules administered are about 200–3000 nucleotides in length and have an average length of about 500. In some embodiments, the compositions contain at least 80% of polynucleotide molecules administered are about 300–2000 nucleotides in length. In some embodiments, the compositions contain at least 80% of polynucleotide molecules administered are about 300–2000 nucleotides in length and have an average length of about 500. In some embodiments, the compositions contain at least 80% of polynucleotide molecules administered are 300–1000 nucleotides in length. In some embodiments, the compositions contain at least 80% of polynucleotide molecules administered are 300–1000 nucleotides in length and have an average length of 500.

In some embodiments, the pharmaceutical compositions are suitable for injection, i.e. sterile and pyrogen free.

EXAMPLE

The foregoing examples are meant to illustrate the invention and are not to be construed to limit the invention in any way. Those skilled in the art will recognize modifications that are within the spirit and scope of the invention. All references cited herein are hereby incorporated by reference in their entirety.

Example 1

Preparations of Human DNA in Cell Medium Change the Pattern of Specific Protein Expression in Human Cancer Cells in Culture Example 1 demonstrates a capability of DNA preparations prepared from healthy donor sperm cells to influence differential expression of specific cell proteins in human tumor cell lines: breast tumor, BT474, ovarian carcinoma OVCAR5 and promielocytic leukemia HL60. The breast tumor cells are adhesive epithelial type cells forming a monolayer with multilayer cell clumps; OVCAR5 are fibroblastoid type cells forming a monolayer and HL60 cells are spherical cells that grow in suspension.

Two types of preparations were used:
1) purified total chromatin prepared from sperm cells and fragmented by nuclease digestion to oligonucleosome size (Wagner, et al. Arch. Androl. (1981) 7(3):251–7, which is incorporated herein by reference) (DNA lengths 200–3000 bp).
2) genomic DNA isolated from sperm cells (using Amersham-Pharmacia 'genomic DNA isolation' kit and procedure modified by addition of a reducing agent (DTT) to lysis buffer) mildly sonicated to obtain 200–3000 bp size fragments.

Cells were plated in 24-well plates for tissue culture at a density of 100,000 cells per well and cultured in RPMI 1640 with addition of 5% fetal calf serum and Pen/strep antibiotics at 37° C. in the presence of 5% $CO_2$ in humidified air.

2 μg of DNA preparations either in the form of DNA solution or as chromatin fragments were added in 20 μl of PBS to all experimental wells, and 20 μl of PBS were added to control wells. The quantity of 2 μg of DNA was chosen in order to provide excess of extracellular DNA over cellular DNA in each well, so that cellular DNA would have a possibility to recombine with extracellular DNA in such manner that all cellular genes (cancerous, normal or mutated) could have a good chance to be substituted at least in part with fragments of normal human extracellular DNA. The medium in wells was changed every 3 days and fresh DNA preparations were also added every 3 days for 2 weeks. Following this incubation period, medium was removed and cells were washed with cold PBS 3 times. Cells were then removed from wells, collected by centrifugation and lysed in sample loading buffer containing 2% SDS, 20% sucrose, 3 mM DTT with incubation of samples on a boiling water bath for 3 min. Samples were resolved in SDS-PAGE and proteins were visualized using an immunoblotting procedure.

Figure 1B:
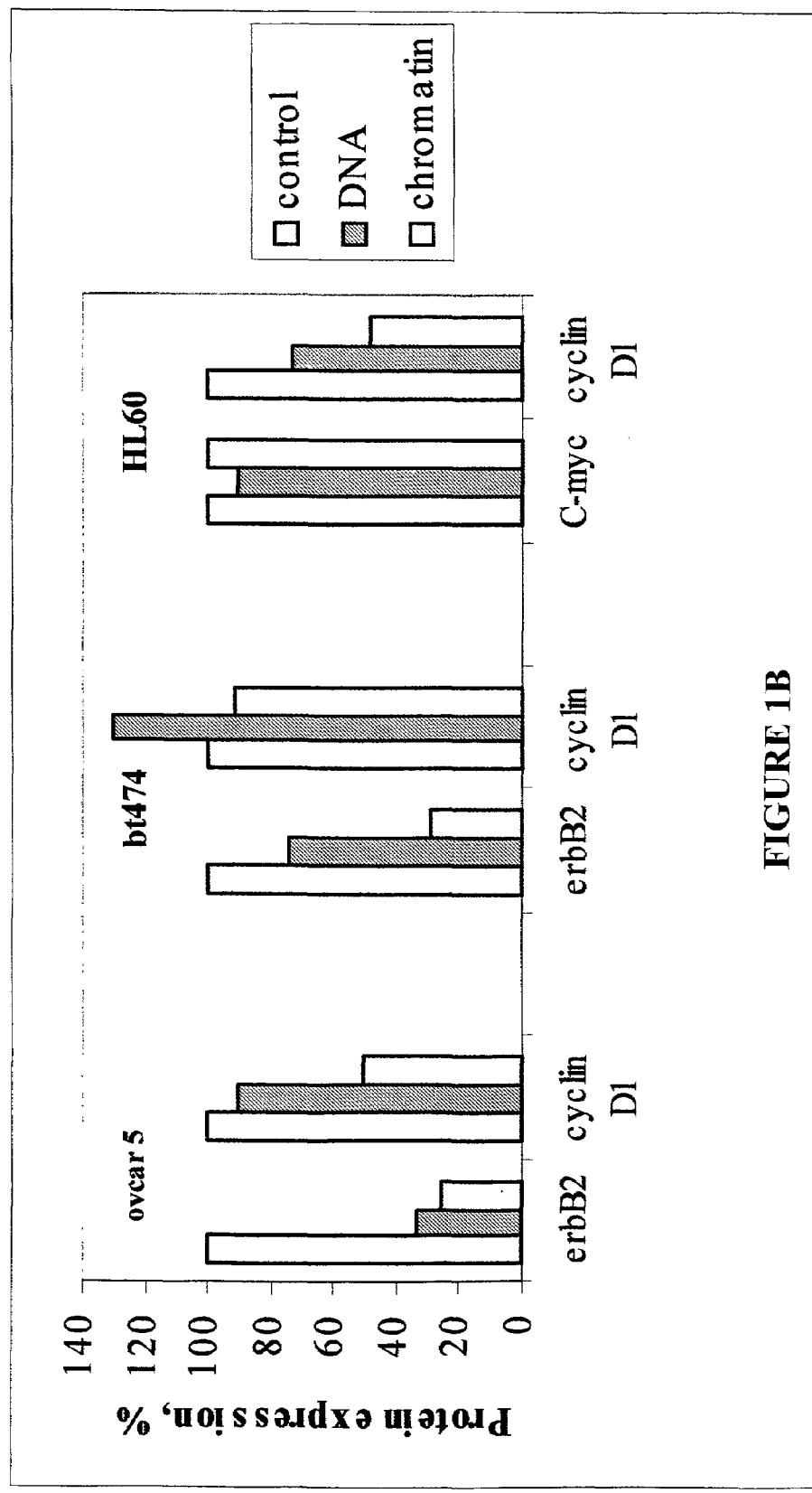
FIG. 1B is a bar graph depicting protein quantitation data corresponding to the data in FIG. 1A.
Figure 2:
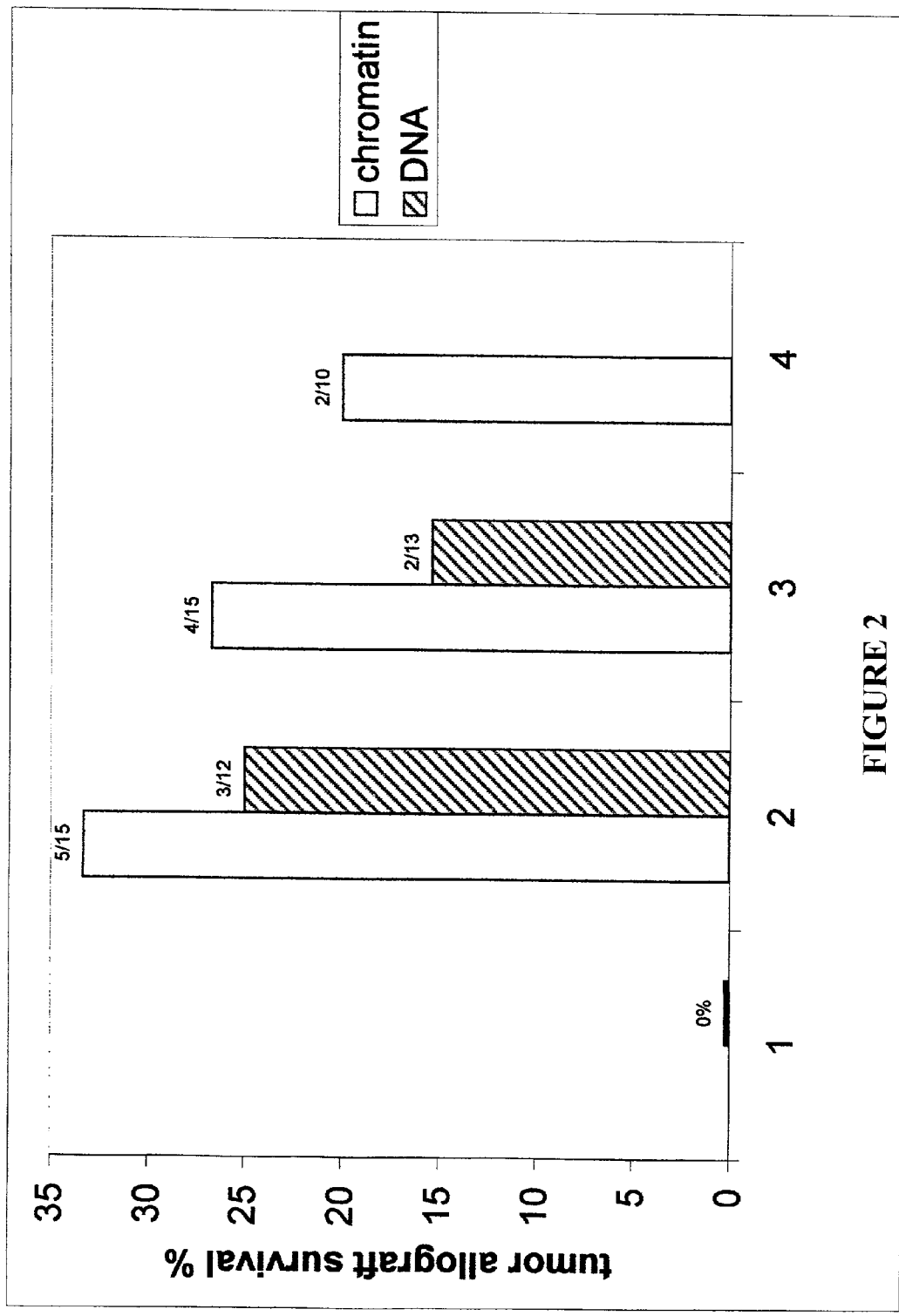
FIG. 2 shows the survival of A/He mouse strain specific tumor allograft in immunologically incompatible CBA mice injected with A/He strain DNA preparations. Two types of preparations were used: 1) A/He purified total chromatin digested by micrococcal nuclease to oligonucleosome size fragments (200–3000 bp DNA) (diamond cross, xxxx). 2) A/He isolated genomic DNA mildly sonicated to obtain 200–3000 bp size fragments (///). The following schemes of DNA treatments were applied to 4 groups of the recipient CBA mice: 1—injection of physiological salt solution (control group); 2—single i.p. injection of either DNA or chromatin preparation (40 µg of DNA per injection in the form DNA and chromatin) on the second day after birth; 3—a series of 4 injections of either DNA or chromatin preparation (40 µg of DNA per injection in the from of DNA or chromatin) every 5 days starting with the second day after birth; 4—a series of 3 injections of chromatin (40 µg of DNA per injection) every 5 days starting from the $6^{th}$ day after birth. Hepatoma A tumors were inoculated into treated and control mice 25 days after single preparation injection or one week after last injection at multi-injectional therapy. In two weeks approximately 30% of mice that received DNA preparations developed cancer at the spot of inoculation.
Figure 3:
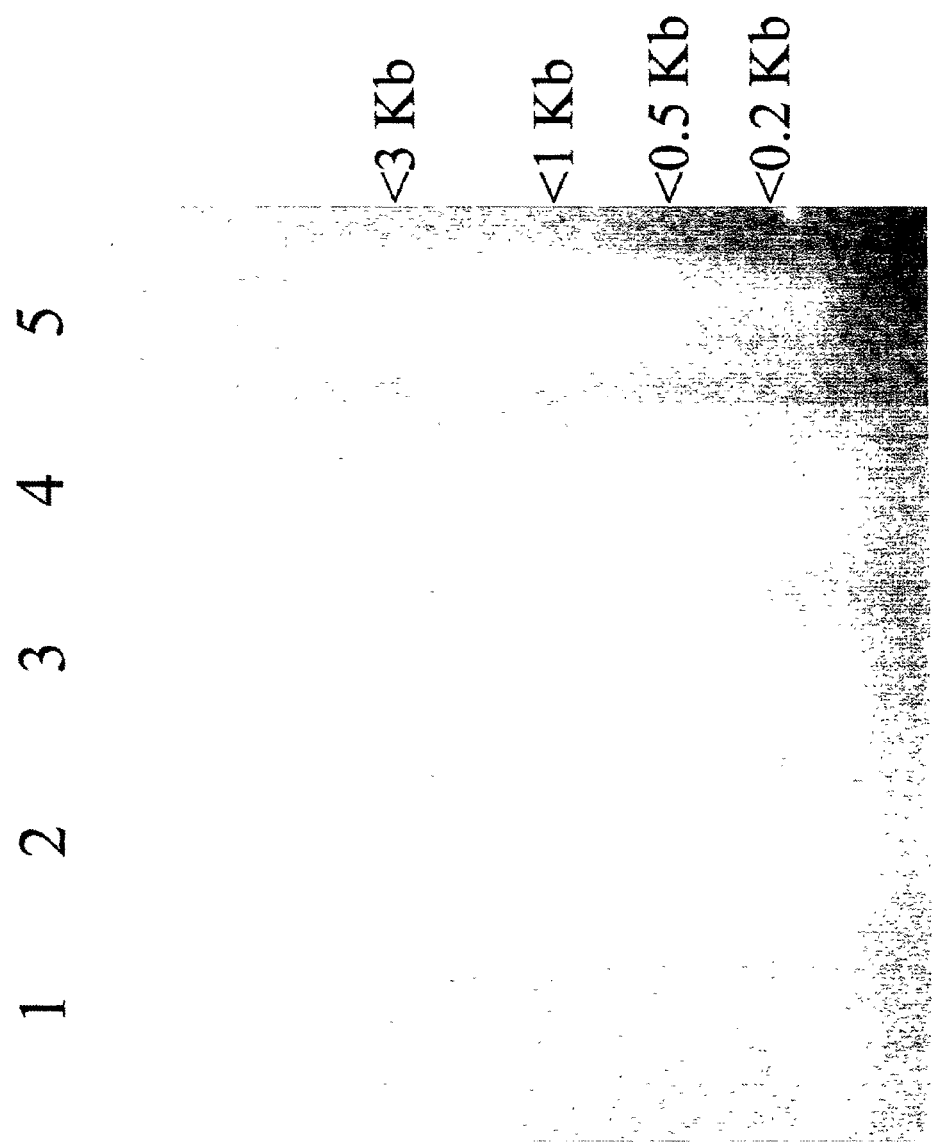
FIG. 3 shows data from random human genomic DNA amplification in PCR reaction. A random primer PCR procedure was used according to Telenius et al. (1992) with modifications. Telenius's 18-mer partially degenerate oligonucleotide primer DOP 6-MW (5'CCGACTCGAGNNNNNNATGTGG SEQ ID NO:1) was used for random DNA amplification in Idaho Technology rapid thermal cycler. Reaction mixture 50 µl contained 1 ng of human DNA, PCR buffer with 0.2 mM $MgCl_2$, 0.2 mM NTP, 2 µM DOP 6-MW and 40 U/ml Taq polymerase. After denaturing of the mixture at 95° C. for 5 min it was incubated 10 sec at 94° C., 10 sec at 53° C. and 30 see at 72° C. for different number of times with final exposure 10 min at 72° C. Samples were resolved in 1% agarose gel in TBE buffer and bands were visualized in UV light after ethydium bromide staining. Lanes are corresponding to: 1 to 15 thermal cycles, 2–25 cycles, 3–35 cycles, 4–45 cycles and 5—molecular weight standards. From the picture one can see that although 15 cycles give low yield, other variants give nearly the same yields of DNA product. Thus using 1 ng of the DNA in a 50 µl reaction mixture we can get up to 10 µg DNA fragments 200–3000 bp in length.

The results are shown in FIGS. 1A and 1B. FIGS. 1A and 1B show that the expression levels of epidermal growth factor family protein erbB2, which is overexpressed considerably in many different types of cancer, dropped down as a result of DNA treatment in OVCAR5 and BT474 cells. In the cell lines OVCAR5 and HL60 our DNA preparations induced considerable downregulation of protein cyclin D1 whose overexpression in cancer cells often correlates with increased proliferation. In contrast, the treatment does not reduce cyclin D1 levels in BT474 cells and may even cause a slight increase. It is noteworthy that BT474 cells are slowly proliferating cells, and may require only a minimal level of cyclin D1 expression that cannot be reduced. The experimental effect appears more pronounced when DNA in complex with basic nuclear proteins (fragmented chromatin) was used as DNA preparation. This can be explained by lesser accessibility of such complexes to nuclease attack in medium or in some cellular compartments. It may also may be due to easier cellular uptake of such complexes. It should also be noted that the choice of two weeks time exposure of cells to extracellular DNA in this experiment was based on preliminary experiments in which we found that treatment with the DNA preparations had no visible toxic effect on cells for at least ten days or more. Furthermore no changes in differential protein expression could be found during first ten days of the experiment. In the following few days (depending on dose) changes in protein expression started to occur, but beyond 20 days, the cells changed their properties so much that it became difficult to maintain cell culture. For example, in BT474 cells the most developed effects were observed in wells with fragmented chromatin; on day 15–16 of the experiment the number of cells in these wells decreased two times compared to the control wells because of the retardation in cell division and death of some cells. Stopping addition of DNA preparations after the 2 weeks' treatment did not help cells detectably: they grew slower and slower. The cells treated with naked DNA also stopped growing, similar to the cells treated with chromatin fragments. We replated these cells, and they attached to plastic, but did not grow well. After a month of such cultivation they were still alive, but did not form a monolayer and their number gradually decreased. This whole pattern looks like the desired solution of many anticancer projects: either make cancer cells die or stop proliferating. Genomic DNA treatment appears to achieve that goal.

Example 2

Introduction of Changes Into Cellular Genomic DNA in Living Mice Induction of Artificial Tolerance in Recipient Mice to a Donor Allograft CBA and A/He are immunologically distinct mouse strains, and A/He allografts to CBA are never accepted but are always quickly rejected (Kaledin, et al. 1974 Conf. of the Res. Lab. of Exp. Biol. Models (Abstracts) Acad. Med. Sci, Moscow USSR p 5–52). The example demonstrates induction of immunological tolerance in CBA mice via injection of appropriate amounts of donor DNA preparations. The supposed mechanism of such induction is that injected donor DNA is substituting responsible alleles in CBA recipient cells to A/He specific alleles. This substitution will result in emergence of A/He antigens on CBA cells, which is probably followed by negative selection of lymphocyte clones normally responsible for the rejection.

A/He mouse strain specific hepatoma A, which is unable to grow in CBA mice mainly because of immunologic incompatibility, was used as tumor allograft for allotransplantation in treated and control CBA mice. $10^6$ tumor cells were inoculated subcutaneously in the lateral part of the hind leg of the recipient CBA mice. The administration of that number of cells results in tumor growth in 100% of the A/He mice over the time of 1 to 2 weeks. This treatment never leads to formation of tumor in CBA mice (Kaledin, et al. 1974 supra). DNA isolated from A/He mice liver and mildly sonicated to obtain fragments with lengths between 200 and 3000 bp and A/He mice liver purified chromatin digested with micrococcal nuclease to oligonucleosome size fragments with DNA length between 200 and 3000 bp were injected i.p. in CBA mice according to three different schemes:

a single i.p. injection of either DNA or chromatin preparation (40 μg of DNA per injection in the form DNA and chromatin) on the second day after birth;

a series of 4 injections of either DNA or chromatin preparation (40 μg of DNA per injection in the from of DNA or chromatin) every 5 days starting with the second day after birth;

a series of 3 injections of chromatin (40 μg of DNA per injection) every 5 days starting from the $6^{th}$ day after birth;

control groups received injections of physiological salt solution.

Hepatoma A tumors were inoculated into treated and control mice 25 days after a single injection, or one week after the last injection in multi-injectional therapy. Two weeks later, approximately 30% of mice that received DNA preparations developed cancer at the site of inoculation. No cancer developed in control groups of mice. It seemed that the DNA in chromatin fragments was slightly more effective in this experiment. In the following next two weeks, the percentage of mice that developed cancer increased to approximately 50% in treated mice.

Although immune incompatibility is considered to be the main cause of rejection of hepatoma A tumor by CBA mice, there are probably other factors that interfere with the tumor acceptance. Usually after allotransplantation one can see healing of seams and wounds during the first 10–12 days before the immune response is developed. Then the immune system rejects the allograft. The inoculation of $10^6$ of tumor cells to the A/He mouse strain resulted in solid tumor development 7–14 days after the treatment, so if the inoculated tumor cells proliferated at the same rate in CBA mice, then at least a small tumor should have appeared in the inoculation site before development of the immune response. It did not happen which means that not only immune problems but some other factors or their absence prevented tumor development in the CBA mice soon after the inoculation. If the latter assumption is true then the genomic DNA therapy enables both: creation of the transplantational tolerance and supplying of the CBA mice with some missing, A/He specific factors that are required for hepatoma A proliferation.

Example 3

Random Human Genomic DNA Amplification in PCR Reaction

We used a random primer PCR procedure mainly according to Telenius et al (1992) supra with modifications. Telenius's 18-mer partially degenerated DOP 6-MW oligonucleotide primer was used for random DNA amplification. The typical protocol was as follows: PCR buffer with 0.2 mM MgCl$_2$, 0.2 mM NTP, 2 µM DOP 6-MW, 40 U/ml Taq polymerase. Cycler: 95° C. 5'; 10" 94° C., 10" 53° C., 30" 72° C. (the latter three steps are repeated 30 times), 10'72° C. Using 1 ng of the DNA in a 50 µl reaction mixture we can get up to 10 µM DNA fragments 200–3000 bp in length. 1 liter mixtures yields 0.2 g DNA, 10 liter mixtures yields 2 g DNA. For 1 liter mixtures we need about 40,000 U Taq polymerase, 100 ml 2 mM NTP (100 mg NTP), 20 ml 100 µM DOP 6 M-W (2 µmol).

Example 4

The present invention includes an apparatus for doing large scale PCR preparations. The apparatus comprises a reaction tube, at least one pump for continuously supplying of reagents to the reaction tube, four temperature chambers, and a collection vessel. The reagents are combined and enter the reaction tube by action of the pump. In some embodiments, there are two supply pumps which combine various components into a mixing vessel which then communicates with the reaction tube. The reaction solution flows through the reaction tube through a series of reaction tube lengths which alternately pass through each of the four temperature chambers to produce a cycle segment. That is, the reaction solution flows through the reaction tube which passes through each of the four temperature chambers. The portion of the reaction tube which passes through each of the four temperature chambers is referred to as a cycle segment and the flow of the reaction solution through a cycle segment corresponds to a cycle. The reaction tube comprises at least twenty consecutive cycle segments. That is the reaction tube emerges from the fourth chamber and reenters the first chamber at least twenty times. In preferred embodiments, the reaction tube comprises at least thirty consecutive cycle segments, in some preferred embodiments, the reaction tube comprises at least forty consecutive cycle segments.

Figure 4:
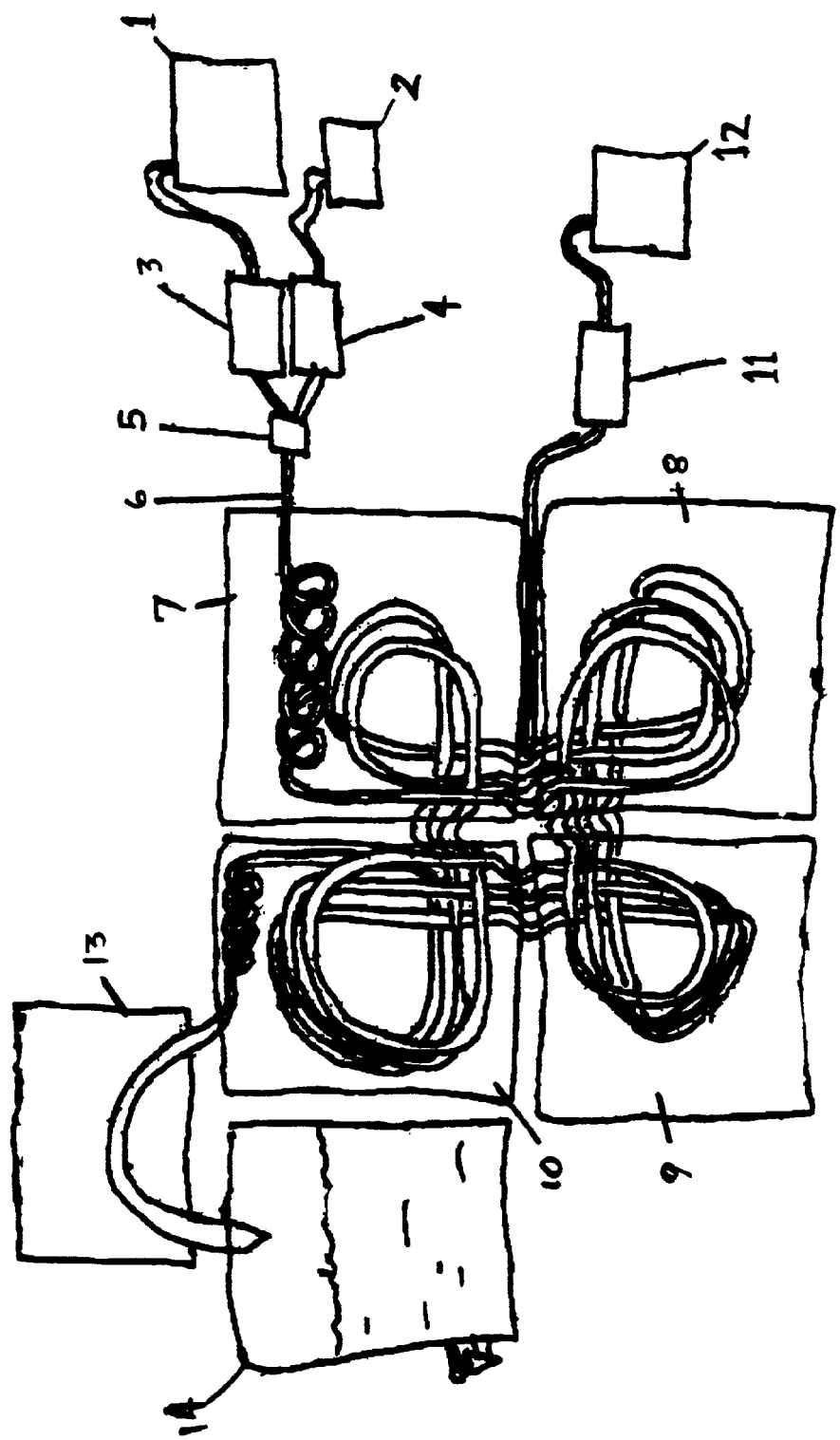
FIG. 4 is a schematic drawing of the apparatus for large scale amplification of genomic DNA as described in Example 4.

In a preferred embodiment the genomic DNA is manufactured as copies using random PCR with partially degenerate primers. As discussed above, in some embodiments such as for example those involving severe genomic diseases, the total dosage for a course of treatment (for a few months) may comprise 10–20 g of DNA. For manufacturing of such amounts of DNA special large scale PCR apparatus is designed and illustrated in FIG. 4.

Appropriate proportions of Solution 1: PCR buffer, nucleoside triphosphates and DNA template in optional Reagent Vessel I (1) and Solution 2: Taq polymerase in optional Reagent Vessel II (2) are preferably first combined using two pumps, Pump I (3) and Pump II (4) and an optional mixing chamber (5) for gradient formation in HPLC. In some embodiments, the mixed solutions are injection into the reaction tubing (6) by way of a single pump (not shown) which may be provided for example after a mixing chamber or, as shown here, optionally using two pumps (3, 4) where the DNA template is amplified in a reactor comprising four thermoregulated circulating water baths (7, 8, 9 and 10). The tubing (6) enters and exits all the four baths (7, 8, 9 and 10) one after another in series which is referred to herein as a cycle. The temperature in the first bath (7) is preferably 95° C. The temperature in the second bath (8), which is referred to as the Cooling Bath I, is preferably 90° C. The temperature in the third bath (9), which is referred to as the Annealing Bath, is preferably 55° C. The temperature in the fourth bath (10) is preferably 72° C. The reaction mixture repeats the cycle for appropriate number of times (typically 30) which is specified in the optimization procedure. The cycle is repeated by the tubing (6) re-entering the bath (7) after emerging from bath (10) then continuing through bath (8), then bath (9), then (10) again and, to repeat back through the temperature chambers again (7, 8, 9 and 10).

The tubing can be made from any material compatible with PCR or its inner surface can be coated with such material. The preferred material is stainless steel or plastic used for medical purposes. The inner diameter of the tubing is between 3 mm and 20 mm, but can also be wider. In some cases when tubing with inner diameter over 4 mm is used a rigid spiral is inserted in the tubing to provide automatic mixing of solutions inside the tubing. Optional Pump III (11) is used for injecting additional quantities of the reagents (NTPs, Taq polymerase) from optional Reagent Vessel III (12) into the main tubing. After the reaction mixture has circulated through the last bath in the last cycle, it optionally moves through Cooling Bath II (12) and further into the tank for storage of the PCR product, the Collection Vessel (13). The temperature in the Cooling Bath II (12) and Collection Vessel (13) is preferably 0° C.

The machine is capable of performing PCR in 50–1000 liter of the reaction volume per day. The apparatus provides for continuous flow of reaction mixture through the various baths. Depending upon the flow speed and length of tube within a given temperature bath, the length of time the reaction mixture will spend at a temperature during a cycle can be determined. The reaction times for each temperature is thus a function of the flow rate and the length of tube within a temperature bath. Various configurations may be employed to achieve the desired lengths within the various temperature baths.

I claim:

1. A method of treating a human individual who has a disease or disorder associated with exposure to ionizing radiation comprising the step of
administering to the individual who has been exposed to ionizing radiation a therapeutically effective amount of a plurality of polynucleotide molecules that are free of vector sequences, wherein
the plurality of polynucleotide molecules collectively comprises an essentially complete human genome derived from autologous DNA collected from the individual before the individual is exposed to the ionizing radiation; and each of the plurality of polynucleotide molecules having about 100–3000 nucleotides.

2. The method of claim 1 wherein the plurality of polynucleotide molecules are free DNA.

3. The method of claim 1 wherein at least 80% of polynucleotide molecules administered are about 200–3000 nucleotides in length.

4. The method of claim 1 wherein at least 80% of polynucleotide molecules administered are about 200–3000 nucleotides in length and have an average length of about 300–1000.

5. The method of claim 1 wherein at least 80% of polynucleotide molecules administered are about 300–2000 nucleotides in length.

6. The method of claim 1 wherein the plurality of polynucleotide molecules are administered in an amount of 0.4–20 g of polynucleotides having 200–3000 nucleotides each.

7. The method of claim 1 wherein the plurality of polynucleotide molecules are administered in an amount of 1–16 g of polynucleotides having 200–3000 nucleotides each.

8. The method of claim 1 wherein the plurality of polynucleotide molecules are administered by a regiment selected from the group consisting of: continuous infusion, multiple doses administered hourly, multiple doses administered daily, multiple doses administered every other day, multiple doses administered weekly.

* * * * *